(12) United States Patent
Minor et al.

(10) Patent No.: US 6,309,403 B1
(45) Date of Patent: Oct. 30, 2001

(54) DEXTEROUS ARTICULATED LINKAGE FOR SURGICAL APPLICATIONS

(75) Inventors: Mark A. Minor, Grand Ledge; Ranjan Mukherjee, East Lansing, both of MI (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

(21) Appl. No.: 09/320,916

(22) Filed: May 27, 1999

Related U.S. Application Data
(60) Provisional application No. 60/087,552, filed on Jun. 1, 1998.

(51) Int. Cl.$^7$ .................................................. A61B 17/28
(52) U.S. Cl. ............................................................ 606/205
(58) Field of Search .................................. 606/205, 170, 606/174, 206, 207, 208; 600/146, 139, 141, 142–151

(56) References Cited

U.S. PATENT DOCUMENTS

| | | |
|---|---|---|
| 5,209,747 | 5/1993 | Knoepfler . |
| 5,251,127 | 10/1993 | Raab . |
| 5,305,203 | 4/1994 | Raab . |
| 5,374,277 | 12/1994 | Hassler . |
| 5,383,888 | 1/1995 | Zvenyatsky et al. . |
| 5,403,342 | 4/1995 | Tovey et al. . |
| 5,409,498 | 4/1995 | Braddock et al. . |
| 5,456,401 | 10/1995 | Green et al. . |
| 5,549,637 | 8/1996 | Crainich . |
| 5,564,615 | 10/1996 | Bishop et al. . |
| 5,607,094 | 3/1997 | Clark et al. . |
| 5,618,294 | * 4/1997 | Aust et al. ............................ 606/170 |
| 5,630,832 | 5/1997 | Giordano et al. . |
| 5,722,988 | 3/1998 | Weisshaupt . |
| 5,748,767 | 5/1998 | Raab . |
| 5,749,893 | 5/1998 | Vidal et al. . |
| 5,810,716 | * 9/1998 | Mukherjee et al. .................. 600/146 |
| 5,810,718 | * 9/1998 | Mukherjee et al. .................. 600/146 |

FOREIGN PATENT DOCUMENTS 42 43 715   12/1992   (DE) .

OTHER PUBLICATIONS

Cohn, M.B. et al., "Surgical Applications of Milli–Robots," *Journal of Robotic Systems* 12(6):401–416 (1995).

(List continued on next page.)

*Primary Examiner*—Henry J. Recla
*Assistant Examiner*—(Jackie) Tan-Uyen T. Ho
(74) *Attorney, Agent, or Firm*—Harness, Dickey & Pierce, P.L.C.

(57) ABSTRACT

A surgical instrument includes an actuator, a tool, and a positioning apparatus. The positioning apparatus includes a gear link structure operably coupling the tool to the actuator for moving the tool in a first direction defining a first degree of freedom and in a second direction defining a second degree of freedom.

21 Claims, 3 Drawing Sheets

OTHER PUBLICATIONS

Dautzenberg, P. et al., "A Powered Dexterous Instrument With Surgical Effectors for Telemanipulator Assisted Laparoscopy," *IEEE–EMBC and CMBEC*, Theme 5: Neromuscular Systems/Biomechanics, pp. 1187–1188 (1995).

Mueglitz, J. et al., "Kinematic Problems of Manipulators for Minimal Invasive Surgery," *End. Surg.* 1:160–164 (1993).

Mukherjee, R. et al., "An Articulated Manipulator for Enhanced Dexterity in Minimally Invasive Surgery," Proc. 18th Annual International Conference of the IEEE Engineering in Medicine and Biology Society, Amsterdam, The Netherlands (1996).

Sastry, S.S. et al., "Milli–robotics for remote, minimally invasive surgery," *Robotics and Autonomous Systems* 21:305–316 (1997).

Schenker, P.S. et al., "A New Robot For High Dexterity Microsurgery," Computer Vision, Virtual Reality & Robotics in Medicine, First International Conference CVR MED'95, p. 115–122 (1995).

Schurr, M.O. et al., "Development of steerable instruments for minimal invasive surgery in modular conception," *Acta chir. belg.* 93:73–77 (1993).

Sturges, Jr. R.H. et al., "A Flexible, Tendon–Controlled Device For Endoscopy," Proceedings of the 1991 IEEE International Conference on Robotics and Automation, Sacramento, California 2582–2590 (Apr. 1991).

Suzumori, K. et al., "Development of Flexible Microactuator and Its Applications to Robotic Mechansims," *Proceedings of the 1991 IEEE International Conference on Robotics and Automation*, Sacramento, California 1622–1627 (Apr. 1991).

* cited by examiner

DEXTEROUS ARTICULATED LINKAGE FOR SURGICAL APPLICATIONS

This application claims benefit of provisional application Ser. No. 60/087,552 filed Jun. 1, 1998.

TECHNICAL FIELD

This invention relates generally to a linkage apparatus for controlling and positioning a member and, more particularly, to a positioning apparatus having a linkage that provides multiple degrees of freedom for positioning and controlling the operation of surgical tools.

BACKGROUND

Surgeons performing minimally invasive surgery (MIS) manipulate surgical tools through the use of long slender instruments inserted through a small port, commonly in the patient's abdomen. To effectively perform these procedures, the surgeon must be able to accurately position and control the surgical instrument through manual or robotic manipulation. The instruments typically include a tool such as forceps or scissors coupled to a positioning apparatus that provides positioning flexibility. Presently available positioning apparatuses provide single segment articulation of the apparatus body in the form of rotational movement up to ninety degrees (90°). Despite this flexibility, current instrumentation does not achieve the arbitrary orientation often required for complex surgical functions, such as suture placement.

The proper positioning of the surgical tool is complicated by several factors including the fact that the port in the patient's abdomen acts as a laterally restrictive pivot point for the body of the positioning apparatus. Additional factors limiting the effectiveness of MIS positioning apparatuses include the failure to provide articulation in more than one degree of freedom causing a lack of dexterity and the inability to approach a surgical site from an arbitrary orientation. Finally, the repeatability and controllability of traditional instruments, and therefore the fine manipulation skills of the surgeon, are further limited by the large actuation forces required by available actuators including push-pull cable, rotary shaft, and gear driven actuators having an excess number of linkages.

Historical MIS devices include the use of an articulated trunk mechanism, steerable channel, or a robot arm. However, each of these instrument positioning techniques have deficiencies that have prevented their widespread acceptance. Early devices were based upon steerable channels that could accommodate small flexible instruments. These channels allowed the instrument to be changed without negatively effecting the port, but were limited by their structural rigidity. Steerable channels are generally too compliant and unable to support sufficient loads.

Available robot arms and articulating trunks lack dexterity and precision. Specifically, articulating trunk mechanisms recently have included multiple hinged segments that provide bidirectional steering capability of up to 180°. Steering is achieved with a series of hinge connected, equal length segments that operate together to define a single degree of freedom. The instrument can approach organs with arbitrary orientation but requires large actuation forces due to force magnification resulting from the instrument's kinematic design. Force magnification is a significant problem in dexterous surgical instrumentation as it restricts the ability of surgeons to perform fine manipulations during manual operation and significantly decreases load capacity.

Presently available trunk mechanisms also may provide rotation and actuation of a surgical tool connected to the end of the device via additional actuating assemblies. Unfortunately, as the force magnification increases with the square of the number of actuating links, the additional actuating assemblies negatively impact the ability of the surgeon to finely manipulate the device. Moreover, the rotation actuators of presently available trunk mechanisms are generally formed of a super elastic alloy which has a low life expectancy under high cyclic strains and which is adversely affected by large angles of deflection.

In view of the above, a need exists for an improved surgical instrument for positioning and operating a surgical tool. The instrument is desirably compact in design while including improved dexterity, fine motion capability, and load capacity when compared to traditional instruments.

SUMMARY OF THE INVENTION

Accordingly, the present invention improves surgical articulation during minimally invasive surgery by providing a positioning apparatus controllable by an actuator to position a surgical tool in three degrees freedom. More particularly, one embodiment of the present invention allows independent articulation, actuation, and rotation of the compact arrangement that allows effective fine motion control by the surgeon.

To achieve the above objects as well as other advantages, the present invention includes a surgical instrument having an actuator, a tool, and a positioning apparatus. The positioning apparatus includes a gear link structure operably coupling the tool to the actuator for moving the tool in a first direction defining a first degree of freedom and in a second direction defining a second degree of freedom.

BRIEF DESCRIPTION OF THE DRAWINGS

A more complete appreciation of the invention and the many attendant advantages thereof will be readily obtained as the same becomes better understood by reference to the following detailed description when considered in connection with accompanying drawings wherein.

DETAILED DESCRIPTION OF THE INVENTION

Figure 1:
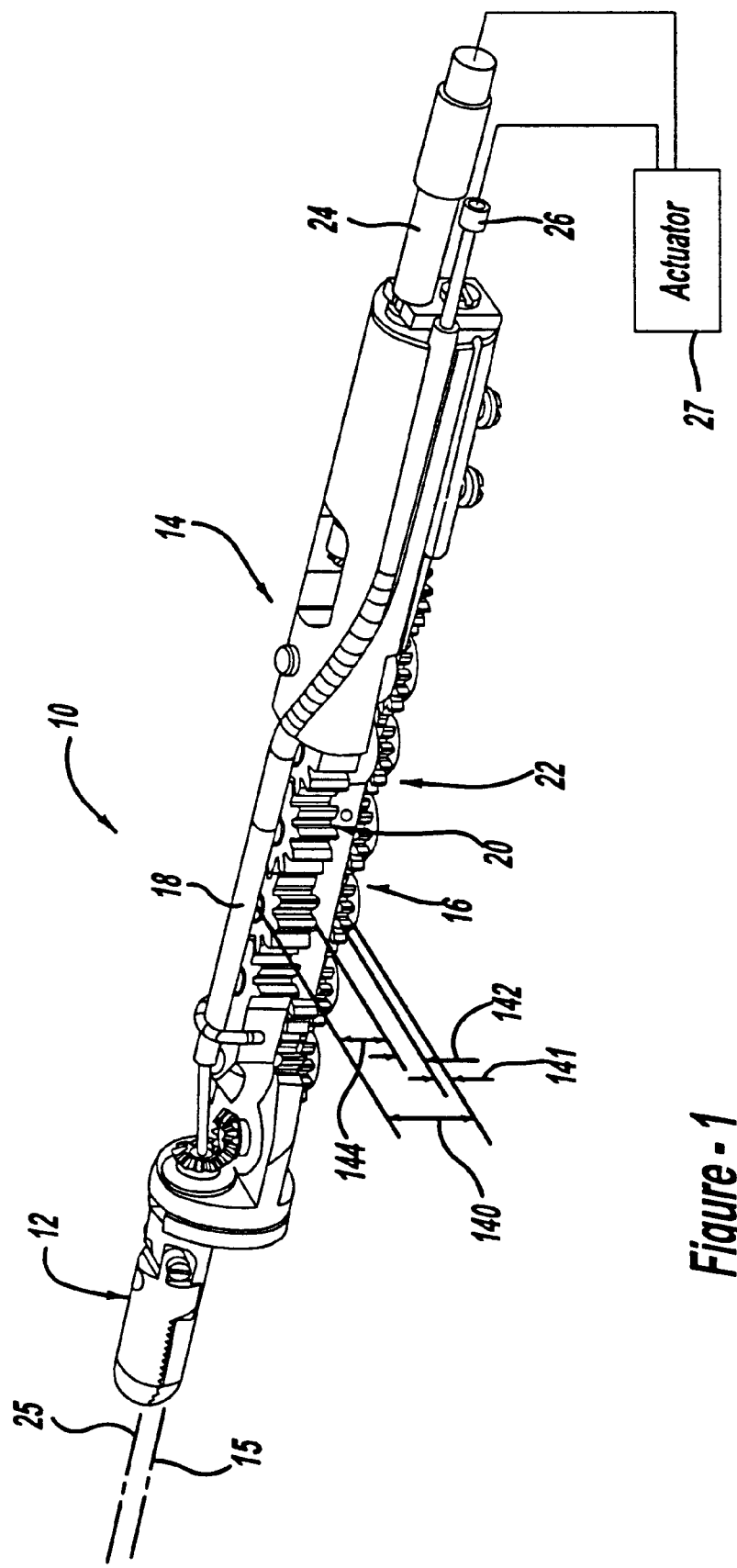
FIG. 1 is an isometric view of the present invention.

As illustrated in FIG. 1, the present invention includes a surgical instrument 10 having a surgical tool 12 operably coupled to a positioning apparatus 14, referred to herein as a dexterous articulated linkage for surgical applications (DALSA), having a longitudinal axis 15. DALSA 14 includes a gear link structure 16 for articulating and rotating tool 12 thereby defining two degrees of freedom for the tool and a cable assembly 18 for actuating the tool and defining a third degree of freedom. More particularly, gear link structure 16 includes a first gear linkage assembly 20 for articulating tool 12, to provide angular displacement from longitudinal axis 15 as indicated by reference numeral 19 (FIG. 3), and a second gear linkage assembly 22 coupled to a drive shaft 24 for rotating tool 12 about a tool axis 25 (FIG. 1).

The structure and operation of DALSA 14, including first and second gear linkage assemblies 20 and 22, will now be described in detail with reference to FIG. 2. Initially, DALSA 14 includes a base link 28 that is configured to accommodate the various drive assemblies of DALSA. Specifically, base link 28 includes a cavity 30 communicating with a bore 34 within which drive shaft 24 is disposed for rotation. Cavity 30 accommodates a pinion assembly 36 having a driving bevel gear 38 that is fixed for rotation with drive shaft 24 and a first pinion bevel gear 39 in meshed engagement with gear 38. As is described in detail below, drive shaft 24 controls rotation of tool 12 via second gear linkage assembly 22.

Figure 3:
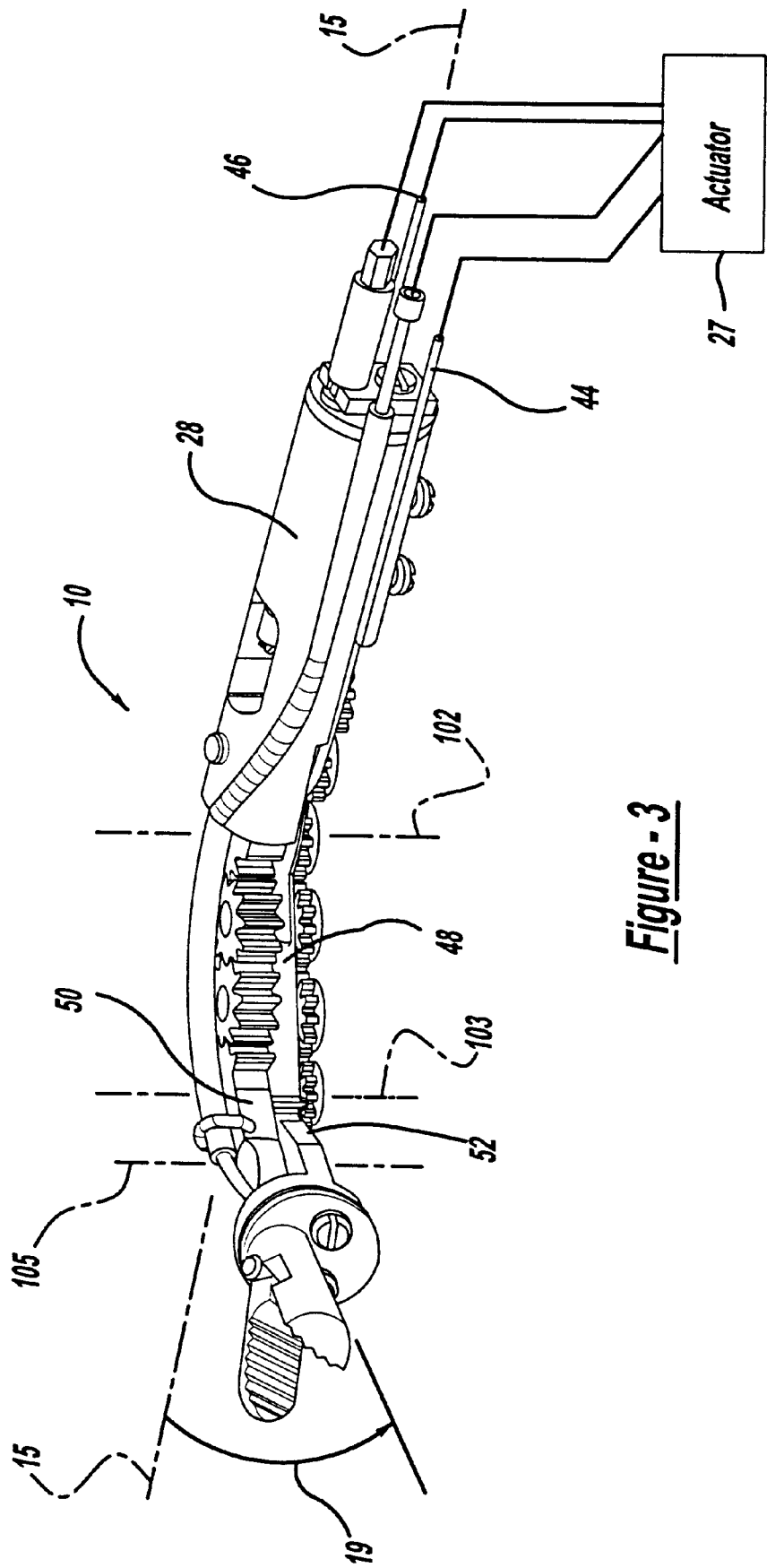
FIG. 3 is an isometric view of the present invention similar to FIG. 1 but illustrating the positioning apparatus in a partially articulated position and the surgical tool in an open position.

Base link 28 also includes a groove 40 formed therein to accommodate cable assembly 18 and a first recess 42 to accommodate a first drive tendon 44 of cable 21 (FIG. 3). Those skilled in the art will appreciate that base link 28 further includes a second recess (not shown) opposite first recess 42 that is sized to accommodate a second tendon 46. First and second drive tendons 44 and 46 control first gear linkage assembly 20 while cable assembly 18 actuates tool 12. The drive shaft 24, drive tendons 44 and 46, and a first end 26 of cable assembly 18 are adapted to be operably coupled to an actuator 27 (FIG. 3) for manipulation by the surgeon.

First gear linkage assembly 20 includes base link 28 as well as a drive link 48, a drag link 50, and a tip link 52. First gear linkage assembly 20 also defines an upper gear pack 53 connecting base link 28 with drag link 50. More particularly, base link 28 includes a gear projection 56 integral with a first end 54 of the base link and formed about a first axis 102. In a similar manner, drag link 50 includes an integral gear projection 58 centered about an axis 103. Base link 28 is mechanically coupled to drag link 50 via spur gears 60 and 62 which are in intermeshed engagement with gear projections 56 and 58, respectively. Each of gears 56, 58, 60, and 62 include an aperture 64 to accommodate one of pins 66, 68, 70, and 72 in a press-fit engagement to couple the gears for rotation with respect to the pins and links.

Drive link 48 includes a plurality of passages 74 that accommodate pins 66, 68, 70, and 72 in a slip-fit engagement. The pins couple gears 56, 58, 60, and 62 to drive link 48 for translational movement therewith while permitting rotational movement of the gears relative to the drive link. First gear linkage assembly 20 also includes a middle gear pack 73 that includes drive link 48 and that couples the drive link with tip link 52. More particularly, drive link 48 includes a smooth faced semicircular first end 76, a geared projection 78 centered about axis 103 and side passages 81 and 83 that extend from and between the side faces, e.g. side face 85, of drive link 48.

Tip link 52 includes an upstanding hub 82 integral with a flat 84 having a geared projection 86 centered about an axis 105. Geared projection 86 forms part of middle gear pack 73. Flat 84 is coupled for rotation relative to drag link 50 via a pin 108. Flat 84 also includes a circular recess 90 extending downwardly from the top face of flat 84 and a passage 92 communicating with recess 90. Hub 82 includes an arrangement for mounting a tool to the DALSA which, in the illustrated embodiment, includes a tool passage 94 and threaded passages 96.

The articulation of DALSA will now be described with reference to FIGS. 1–3. DALSA articulation is controlled by the axial displacement of tendons 44 and 46 and the corresponding movement of a first gear linkage assembly 20. As is best illustrated in FIG. 2, tendons 44 and 46 are wrapped about a grooved idler pulley 98 that is coupled to base link 28 by a slip-fit engagement with a pin 100. First tendon 44 is disposed through side passage 83 and retainingly engages side face 85 such as by forming a knot or stop to engage the side face. Second tendon 46 is disposed through side passage 81 and retainingly engages a side face of drive link 48 that is opposite side face 85 in a manner similar to that described above. Those skilled in the art will appreciate that drive link 48 is rotated about the axis 102 of pin 66 upon axial displacement of first or second tendons 44 and 46. It should also be appreciated that first end 76 of drive link 48 is provided with a constant radius surface that along with the wrapping of the tendons about the idler pulley ensures that the tendons will remain in contact with first end 76 and that the ratio of the longitudinal displacement of the tendons relative to the angular displacement of drive link 48 remains constant through the range of operative movement of the DALSA.

When drive link 48 is translated relative to axis 15 (FIG. 1) in the direction of arrow 19 (FIG. 3) and arrow 104 (FIG. 2) about axis 102 in a counterclockwise direction when the DALSA is viewed from above, gears 58, 60, and 62 are translated with drive link 48. The intermeshed relationship of gears 56, 60, 62, and 58 and the angular displacement of link 48 causes gear 60 to rotate counterclockwise about pin 68 and in a planetary motion about geared projection 56. Similarly, gear 62 rotates clockwise about pin 70 and gear 58 counterclockwise about pin 72 and axis 103. The rotation of gear 58 about axis 103 angularly displaces a second end 106 of drag link 50 counterclockwise. Finally, the intermeshed engagement of geared projection 78 of drive link 48 with the geared projection 86 of tip link 52 causes geared projection 86 to rotate in a planetary fashion about geared projection 78 as second end 106 of drag link 50 is displaced relative to drive link 48. The planetary movement of geared projection 86 angularly displaces upstanding hub 82 of tip link 52 counterclockwise relative to pin 108 and about axis 105.

FIG. 3 illustrates the surgical instrument 10 in a partially actuated position where drive link 48 is angularly displaced relative to base link 28 about axis 102, drag link 50 is angularly displaced relative to drive link 48 about axis 103, and tip link 52 is angularly displaced relative to drag link 50 about axis 105. Those skilled in the art will appreciate that the magnitude of the angular displacement about axes 102, 103, and 105 relative to the longitudinal displacement of tendons 44 and 46 is governed by, among other factors, the number and pitch of the gear teeth. In the preferred embodiment, as mentioned above, the wrapping of the tendons 44 and 46 about pulley 98 and end 76 of drive link 48 results in a linear relationship between tendon displacement and link rotation. Moreover, the gears are configured to provide the same angular displacement about axes 102, 103, and 105 such that displacement of drive link 48 beta degrees relative to base link 28 about axis 102 causes an angular displacement of beta degrees about axes 103 and 105 thereby resulting in a total angular displacement of tip link 52 relative to base link 28 of three beta degrees. Those skilled in the art will appreciate that the present invention may be modified to provide varying angular displacements without departing from the scope of the invention as defined by the appended claims.

From the above description, those skilled in the art will appreciate that DALSA is based upon a driven and driving gear linkage structure wherein each segment of the linkage is both a driven link and a driving mechanism. Moreover, while actuator 27 is illustrated as being the controller for DALSA 14, those skilled in the art will appreciate that robotic controls may be included with the actuator. More particularly, a slave external support robot can provide precise positioning and orientation of DALSA relative to the surgery port. Surgeon control of the system can be accomplished by a master robot surgeon interface, which possesses kinematic degrees of freedom corresponding intuitively to surgical member degrees of freedom. It is also contemplated that DALSA may be provided with visual and/or force sensing feedback to provide real time feedback to the surgeon as to the location of, and forces exerted on, the tool.

In addition to the articulation control provided by first gear linkage assembly 20, the present invention includes an additional linkage of independently operating gears creating an additional degree of freedom in the structure without significant increases in space requirements or necessitating modifications in current surgical techniques.

Augmenting the structure further with more linkages of gears allows successive degrees of freedom to be created. The number of degrees of freedom is limited only by the thickness of each gear layer and the desired net thickness of the structure. Other advantages of the DALSA design include improved load capacity, dexterity, fine motion capability, and maximization of available work space. These features can be attributed, at least in part, to the geared link configuration which permits 180° articulation while using as few links as possible. Fewer links means that there will be less force magnification and hence the forces will be easier to control. Geared links enhance these features further by providing a high capacity method of transmitting force which is rigid, durable, and easily controlled. Controllability is further enhanced by precise control of dimensional tolerances. Thus, the DALSA provides the surgeon with the ability to approach tissue, either manually or with a robotic system, at arbitrary orientations through 180° bidirectional articulation, unlimited surgical member rotation, and actuation of the surgical member. The rotation and actuation of the surgical tool is discussed below.

As is generally discussed above, second gear linkage assembly 22 provides a rotational degree of freedom for tool 12 in addition to the above described articulation. Second gear linkage assembly 22 includes the above described driving bevel gear 38 and first pinion bevel gear 39, a second pinion bevel gear 110, tool bevel gear 112, and a bottom gear pack 109 that includes spur gears 114, 115, 116, 117, 118, 119, 120, and 121. The driving bevel gear 38 is connected for rotation with drive shaft 24 for driving the second gear linkage assembly 22. The first pinion bevel gear 39 is orthogonally disposed relative to, and meshes with, the driving bevel gear 38 while the first spur gear 114 is coupled for rotation with the first pinion bevel gear 39 such as by a press-fit engagement.

Each of gears 114–121 are in intermeshed engagement with one another to transfer rotational movement of gear 114 to gear 121. The second pinion bevel gear 110 is rotationally coupled with the spur gear 121. Finally, the tool bevel gear 112 is perpendicularly disposed relative to and meshes with the second pinion bevel gear 110 and is coupled to the tool 12. Washers 111 and 113 are disposed about pinion bevel gears 39 and 110 to properly space the gears within cavity 30 and recess 90, respectively.

While the preferred embodiment of the present application uses the second degree of freedom provided by gear linkage assembly 22 for rotation of the surgical member, many other methods of exploiting the additional degree of freedom are available. For example, the linkage could provide individual control over the articulation angle of a specific segment, e.g. tip link 52. This alternative use would allow further control of the articulated shape and hence further access to difficult-to-reach locations. The additional degree of freedom also enables application of the linkage to anthropomorphic situations such as artificial limbs or robot graspers.

Cable assembly 18 actuates the tool between a closed position such as is illustrated in FIG. 1 and an open position such as is illustrated in FIG. 3. Those skilled in the art will appreciate that while a variety of devices may be used to provide this function without departing from the scope of the invention as defined by the appended claims. The illustrated embodiment of DALSA 14 includes cable assembly 18 which is positionable relative to base link 28 and gear linkage assemblies 20 and 22 so as to further satisfy the need for a compact yet efficient surgical instrument.

Figure 2:
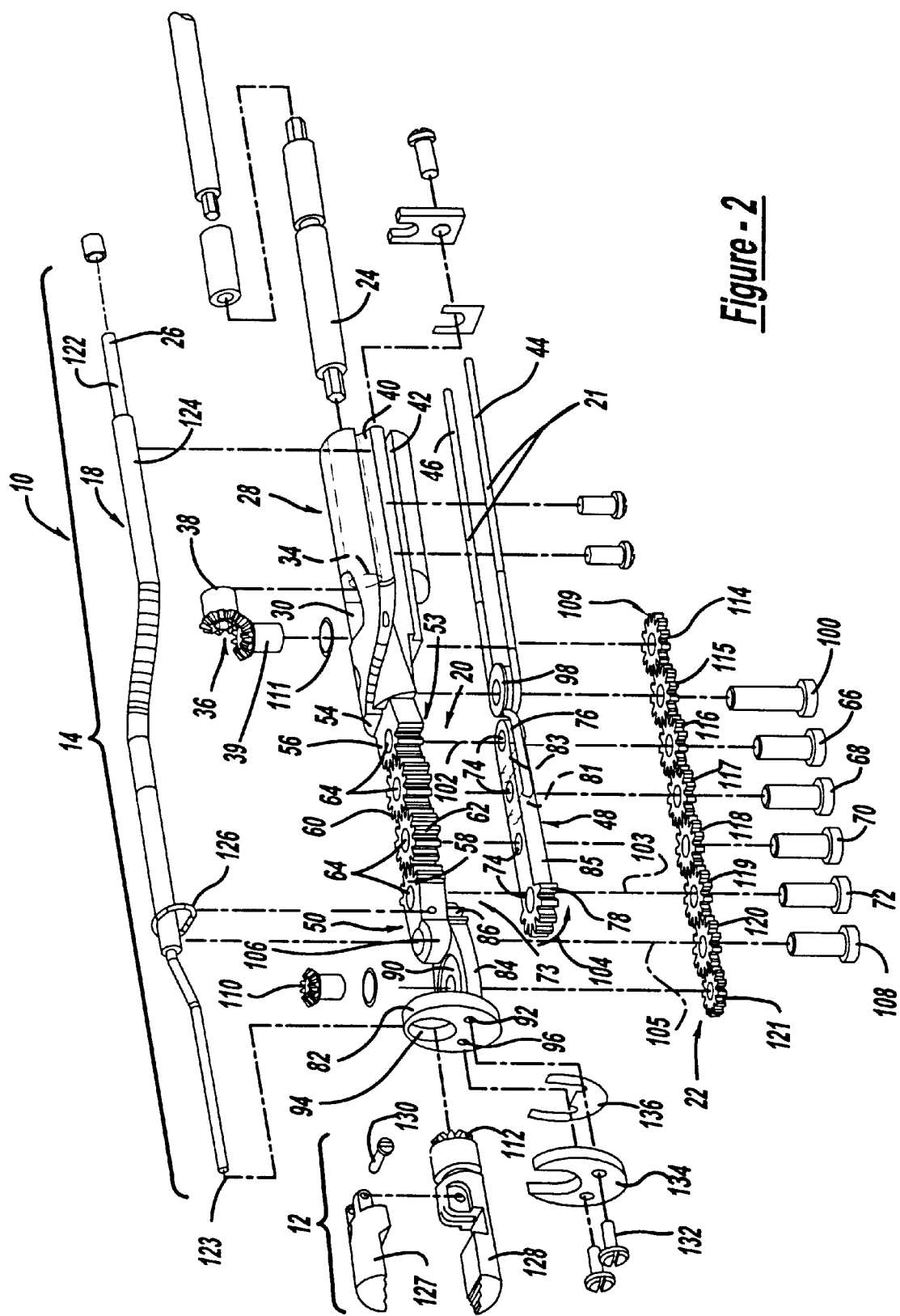
FIG. 2 is an exploded view of the linkage associated with the present invention generally illustrated in FIG. 1.

Cable assembly 18 is illustrated in FIG. 2 to include a cable 122 having first end 26 and a second end 123. Cable 122 is protected by a sheath 124 within which the cable is disposed for axial movement. As discussed above, first end 26 of cable 122 is connectable to the actuator 27 such that axial displacement of cable 122 causes manipulation of tool 12. More particularly, second end 123 is coupled to tool 12 to translate axial movement of cable 122 to the tool. As illustrated, sheath 124 and cable 122 are disposable within groove 40 in base link 28, positionable adjacent upper gear pack 53 and secured to the drag link 50 such as by a clip 126. By taking advantage of the available space adjacent the upper gear pack, cable assembly 18 provides actuation of the tool 12 without significantly increasing space requirements. Moreover, space remaining adjacent to the linkages leaves sufficient room to route cables and tubes desirable for member actuation, force sensing, imaging, or irrigation.

In the illustrated embodiment, tool 12 is shown as forceps having a movable jaw 127 pivotably coupled to a stationary jaw 128 via a pivot pin 130. Second end 123 of cable 122 is coupled to movable jaw 127 such that axial displacement of second end 123 toward base link 28 causes movable jaw 127 to pivot about pin 130 toward an open position. Stationary jaw 128 is coupled to upstanding hub 82 of tip link 52 via threaded fasteners 132 and positioning plate 134. A spacer 136 may be used to adjust the position of tool 12 and thereby gear 112 thereof relative to bevel gear 110. Those skilled in the art will appreciate that a variety of spacer thicknesses may be used to ensure smooth mechanical interaction between bevel gears 110 and 112.

In the illustrated embodiment, the shaft of DALSA can pass through a ten millimeter (10 mm) port and is capable of safely exerting forces at the surgical member on the order of one pound. The illustrated embodiment of the invention is specifically designed to maximize performance of the DALSA mechanism during the manipulation of a one (1) centimeter needle. The specific gear pack thicknesses have been optimized for this application to equally distribute stresses within the respective linkages and maximize the overall load and carrying capabilities of the mechanism. For this specific application, the invention includes an overall gear pack thickness 140 (FIG. 1) of less than approximately 5.5 mm with the bottom gear pack thickness 141 being about 0.88 mm, the middle gear pack thickness 142 being about 1.88 mm, and the top gear pack thickness 144 being about 2.75 mm. Those skilled in the art will appreciate that the thickness of the respective gear packs may vary based upon the specific application if optimization of the stress distribution and load capacity is desired.

The configuration of the gears in the preferred embodiment of the present invention have been specifically designed to increase the load capacity of the DALSA while each of the gears are preferably formed of involute spur gears, the gear profile of the lower gear pack includes a twenty-five (25°) degree pressure angle to the profile and a sixty four (64) diametral pitch and the middle and top gear packs having twenty five degree (25°) pressure angles and a forty eight (48) diametral pitch tooth profile. The larger diametral pitch on the lower gear pack allows gear 121 to have only twelve (12) teeth and thereby a smaller size without an undue risk of undercutting. The smaller size of gear 121 allows the length of the tip link 52 to be decreased thereby increasing load capacity of the DALSA. In the preferred embodiment, the lengths of drive link 48 between axes 102 and 103, drag link 50 between axes 103 and 105, and tip link 52 between the end face of hub 82 and axis 105, respectively, are on the order of 19.1 mm, 6.35 mm, and 10.8 mm. The above design criteria allows DALSA 14 to have a reachable work space of 206 cm$^2$, a dexterous work space of 72 cm$^2$, force magnification on the order 28, backlash of 4 units, an average path curvature of 29.4 mm and a maximum articulatable angle per link of sixty degrees (60°). While the above design has proven to increase the effectiveness of the present invention, those skilled in the art will appreciate that the present invention may be modified for specific applications without departing from the scope of the invention as defined by the appended claims.

In operation, articulation of the apparatus, rotation of the tool, and actuation of the tool can all be independently controlled via actuator 27. In the preferred embodiment of the present invention, the linkages are constructed of tempered UNS S42000 stainless steel with a yield strength of 1480 MPa with a safety factor of 2.0, yielding a short term load capacity approaching 9 N. The maximum stresses in the upper gear pack 53, middle gear pack 73, and bottom gear pack 109 are each on the order of 400 MPa in order to optimize material distribution and distribute the stresses within the material thereby maximizing the load capacity of the DALSA. Finally, the tendons 44 and 46 are preferably formed of Vectran, manufactured by Cortland Cable of Cortland, N.Y. providing a 800 N tensile strength with a safety factor of 2.7 while supporting the maximum load.

While the above description identifies numerous materials and dimensions of the positioning apparatus 14 for use with the preferred embodiment thereof, those skilled in the art will appreciate that the materials and dimensions may be modified without departing from the scope of the invention as defined by the appended claims. Notwithstanding the available departures from the disclosed embodiment, those skilled in the art will further appreciate that the present invention provides a surgical instrument for minimally invasive surgery that includes a positioning apparatus for controllably positioning a surgical tool within three degrees of freedom including independent articulation, actuation, and rotation of the tool. The device satisfies surgical needs for a compact positioning device capable of fine motion control and high load capacities.

What is claimed is:

1. A surgical instrument comprising:
    an actuator;
    a tool; and
    a positioning apparatus including a gear link structure having a first gear linkage assembly operably coupling said tool to said actuator for moving said tool in a first direction defining a first degree of freedom and a second gear linkage assembly operably coupling said tool to said actuator for moving said tool in a second direction defining a second degree of freedom;
    wherein said positioning apparatus further includes a tool actuating assembly coupling said tool to said actuator to move said tool in a third direction defining a third degree of freedom, and said tool actuating assembly further includes a cable located adjacent said first gear linkage assembly.

2. The surgical instrument of claim 1 wherein said positioning apparatus defines a longitudinal axis and movement of said tool within said first degree of freedom includes angular displacement of said tool relative to said longitudinal axis.

3. The surgical instrument of claim 1 wherein said first gear linkage assembly includes:
    a first link;
    a second link;
    a first gear pack coupling said first link and said second link;
    a third link coupled to said second link for rotation relative thereto;
    a fourth link coupled to said first link for rotation relative thereto; and
    a second gear pack coupling said fourth link and said third link.

4. The surgical instrument of claim 1 wherein said first gear linkage assembly includes:
    a first link having a first gear centered about a first axis;
    a second link having a second gear centered about a second axis, said second link coupled to said first link for rotation about said first axis;
    a third link having a first end and a second end, a third gear at said first end and centered about a third axis, said third link coupled to said second link such that said third axis aligns with said second axis;
    a fourth link having a first end and a second end, a fourth gear at said first end of said fourth link and centered about a fourth axis, said fourth gear intermeshed with said second gear, said tool coupled to said second end of said fourth link, and said fourth link coupled to said third link for rotation about said fourth axis; and
    a planet gear coupled to said second link for translation therewith and for rotation relative thereto, said planet gear in meshed engagement with said first gear for planetary movement relative thereto, said planet gear coupled to rotatably drive said third gear, whereby rotation of said second link about said first axis causes angular displacement of said second gear, said planet gear, and said third gear relative to said first axis, whereby said angular displacement of said planet gear relative to said first axis causes planetary rotation of said planet gear about said first gear thereby driving rotation of said third gear about said third axis, whereby rotation of said third gear causes angular displacement of said second end of said third link about said third axis whereupon said fourth gear planetarily rotates about said second gear causing said fourth link to rotate about said fourth axis.

5. The surgical instrument of claim 1 wherein said tool defines a tool axis and movement of said tool within said second degree of freedom includes rotation of said tool about said tool axis.

6. A surgical instrument comprising:
    an actuator;
    a tool; and
    a positioning apparatus including a gear link structure operably coupling said tool to said actuator which operably moves said tool in a first direction defining a first degree of freedom and in a second direction defining a second degree of freedom;

wherein said gear link structure includes a first gear linkage assembly operably coupling said tool to said actuator for movement in said first degree of freedom and a second gear linkage assembly operably coupling said tool to said actuator for movement in said second degree of freedom; and wherein said second gear linkage assembly includes a gear pack with a first gear and a second gear, said actuator rotatably driving said first gear, said first gear rotatably driving said second gear, said second gear is coupled to said tool to move said tool in said second degree of freedom, and at least one of said gear linkage assemblies include a bevel gear.

7. The surgical instrument of claim 1 wherein said tool includes a first jaw pivotably movable relative to an adjacent second jaw.

8. The surgical instrument of claim 7 wherein said actuator includes a drive shaft, said second gear linkage assembly further including a first coupler gear coupling said first gear to said drive shaft to rotate said first gear upon rotation of said drive shaft and a second coupler gear coupling said second gear to said tool to rotate said tool upon rotation of said second gear.

9. The surgical instrument of claim 8 wherein said first coupler gear includes a first bevel gear and a second bevel gear, said first bevel gear coupled for rotation with said drive shaft, said second bevel gear in intermeshed engagement with said first bevel gear and coupled for rotation with said first gear.

10. An apparatus for positioning a tool relative to a workpiece, said apparatus comprising:
  a base;
  a tip;
  a coupling attaching said tool to the tip;
  a first gear linkage coupling said tip to said base in order to move said tip in a first direction relative to said base; and
  a second gear linkage operably moving one of said tip and tool in a second direction relative to said base, at least one of said gear linkages having a first gear and a second gear, said second gear coupling said second gear linkage to said tool, at least one of said gears being a bevel gear.

11. The apparatus of claim 10 wherein said base defines a longitudinal axis and movement of said tip in said first direction includes angular displacement of said tip relative to said longitudinal axis.

12. The surgical instrument of claim 10 wherein said first gear linkage includes:
  a first link having a first gear centered about a first axis;
  a second link having a second gear centered about a second axis, said second link coupled to said first link for rotation about said first axis;
  a third link having a first end and a second end, a third gear at said first end and centered about a third axis, said third link coupled to said second link such that said third axis aligns with said second axis;
  a fourth link having a first end and a second end, a fourth gear at said first end of said fourth link and centered about a fourth axis, said fourth gear intermeshed with said second gear, said tool coupled to said second end of said fourth link, and said fourth link coupled to said third link for rotation about said fourth axis; and
  a planet gear coupled to said second link for translation therewith and for rotation relative thereto, said planet gear in meshed engagement with said first gear for planetary movement relative thereto, said planet gear coupled to rotatably drive said third gear, whereby rotation of said second link about said first axis causes angular displacement of said second gear, said planet gear, and said third gear relative to said first axis, whereby said angular displacement of said planet gear relative to said first axis causes planetary rotation of said planet gear about said first gear thereby driving rotation of said third gear about said third axis, whereby rotation of said third gear causes angular displacement of said second end of said third link about said third axis whereupon said fourth gear planetarily rotates about said second gear causing said fourth link to rotate about said fourth axis.

13. The surgical instrument of claim 10 wherein said second gear linkage includes said first gear and said second gear, an actuator rotatably driving said first gear, said first gear rotatably driving said second gear, and said second gear coupled to said one of said tool and tip.

14. The surgical instrument of claim 13 wherein said actuator includes a drive shaft, said second gear linkage assembly further including a first coupler gear coupling said first gear to said drive shaft to rotate said first gear upon rotation of said drive shaft and a second coupler gear coupling said second gear to said tool to rotate said tool upon rotation of said second gear.

15. The surgical instrument of claim 14 wherein said first coupler gear includes a first bevel gear and a second bevel gear, said first bevel gear coupled for rotation with said drive shaft, said second bevel gear in intermeshed engagement with said first bevel gear and coupled for rotation with said first gear.

16. A surgical instrument comprising:
  an actuator;
  a base;
  a tool coupled to said base;
  a gear assembly including a first gear linkage and a second gear linkage, said first gear linkage coupling said tool to said actuator for moving said tool in a first direction relative to said base, said first gear linkage including a top gear pack in meshed engagement with a middle gear pack, said second gear linkage coupling said tool to said actuator for moving said tool in a second direction relative to said base, said second gear linkage including a bottom gear pack coupled to said actuator.

17. The surgical instrument of claim 16 wherein said gear assembly has a thickness of less than approximately 5.5 millimeters.

18. The surgical instrument of claim 17 wherein said top gear pack has a thickness of about 2.75 millimeters, said middle gear pack has a thickness of about 1.88 millimeters, and said bottom gear pack has a thickness of about 0.88 millimeters.

19. The surgical instrument of claim 16 wherein said tool includes a first jaw pivotably movable relative to an adjacent second jaw.

20. The surgical instrument of claim 19 wherein said jaws define forceps.

21. The surgical instrument of claim 19 wherein said jaws are axially rotatable about a longitudinal axis.

* * * * *